(12) United States Patent
Lore et al.

(10) Patent No.: US 10,163,014 B2
(45) Date of Patent: Dec. 25, 2018

(54) METHOD FOR MONITORING THE VISUAL BEHAVIOR OF A PERSON

(71) Applicant: Essilor International, Charenton-le-Pont (FR)

(72) Inventors: Marie Lore, Charenton-le-Pont (FR); Marion Swital, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 128 days.

(21) Appl. No.: 15/085,450

(22) Filed: Mar. 30, 2016

(65) Prior Publication Data

US 2016/0292517 A1 Oct. 6, 2016

(30) Foreign Application Priority Data

Apr. 2, 2015 (EP) .................................... 15305497

(51) Int. Cl.
| | | |
|---|---|---|
| *G06K 9/00* | (2006.01) | |
| *G06K 9/20* | (2006.01) | |
| *G02B 27/00* | (2006.01) | |
| *A61B 5/18* | (2006.01) | |
| *A61B 5/11* | (2006.01) | |
| *A61B 3/113* | (2006.01) | |
| *A61B 5/00* | (2006.01) | |

(52) U.S. Cl.
CPC .......... *G06K 9/00791* (2013.01); *A61B 3/113* (2013.01); *A61B 5/1128* (2013.01); *A61B 5/6803* (2013.01); *G02B 27/0093* (2013.01); *G06K 9/00335* (2013.01); *G06K 9/00604* (2013.01); *G06K 9/2018* (2013.01); *A61B 5/1123* (2013.01); *A61B 5/18* (2013.01)

(58) Field of Classification Search
None
See application file for complete search history.

(56) References Cited

U.S. PATENT DOCUMENTS

| | | | |
|---|---|---|---|
| 2002/0116156 A1* | 8/2002 | Remboski | G07C 5/0808 702/188 |
| 2002/0188219 A1* | 12/2002 | Suchard | A61B 5/18 600/558 |
| 2005/0203881 A1* | 9/2005 | Sakamoto | G06F 21/552 |
| 2006/0055546 A1* | 3/2006 | Farbos | A61B 3/113 340/575 |

(Continued)

*Primary Examiner* — Reza Aghevli
(74) *Attorney, Agent, or Firm* — Oblon, McClelland, Maier & Neustadt, L.L.P.

(57) ABSTRACT

The disclosed embodiments include a method for monitoring the visual behavior of a person. In one embodiment, the method includes a person activity data providing step during which person activity data indicative of an activity of the person are provided; a person visual behavior data providing step during which person visual behavior data indicative of the visual behavior of the person related to said activity of the person are provided; reference visual behavior providing step during which a reference visual behavior data indicative of the reference visual behavior of the person based on said activity of the person are provided; and a comparing step during which the person visual behavior data and the reference visual behavior data are compared so as to deduce whether the person visual behavior is adapted with respect to said activity of the person.

16 Claims, 3 Drawing Sheets

(56) References Cited

U.S. PATENT DOCUMENTS

| | | | |
|---|---|---|---|
| 2006/0203197 A1* | 9/2006 | Marshall | A61B 3/112 351/246 |
| 2011/0007275 A1* | 1/2011 | Yoo | A61B 3/113 351/209 |
| 2013/0091539 A1* | 4/2013 | Khurana | G06F 21/552 726/1 |
| 2013/0144919 A1* | 6/2013 | Firminger | G06Q 10/10 707/803 |
| 2013/0291099 A1* | 10/2013 | Donfried | G06Q 30/0637 726/22 |
| 2013/0293844 A1* | 11/2013 | Gross | A61B 3/0025 351/209 |
| 2014/0347479 A1* | 11/2014 | Givon | G06K 9/00342 348/143 |
| 2015/0213391 A1* | 7/2015 | Hasan | G06Q 10/06398 705/7.42 |

* cited by examiner

METHOD FOR MONITORING THE VISUAL BEHAVIOR OF A PERSON

FIELD OF THE INVENTION

The invention relates to a method for monitoring the visual behavior of a person and to a method for determining a reference visual behavior corresponding to an activity of a person. The invention further relates to system for monitoring the visual behavior of a person.

BACKGROUND OF THE INVENTION

Some activities require a great degree of concentration. It has been observed that a change in behavior upon carry out an activity may lead to very different results in terms of achievement of the activity.

For example, when carrying out sport, the body behavior of the person may have great influence on the sports results.

Therefore, there is a need for a method for monitoring the behavior of a person relative to the activity carried out by said person.

One object of the present invention is to provide such a method and a system allowing such monitoring.

SUMMARY OF THE INVENTION

To this end, the invention proposes a method, for example implemented by computer means, for monitoring the visual behavior of a person, the method comprises:
- a person activity data providing step during which person activity data indicative of an activity of the person are provided,
- a person visual behavior data providing step during which person visual behavior data indicative of the visual behavior of the person related to said activity of the person are provided,
- an environment data providing step during which environment data indicative to the environment of the person are provided,
- reference visual behavior providing step during which a reference visual behavior data indicative of the reference visual behavior of the person based on said activity of the person and the environment data are provided,
- a comparing step during which the person visual behavior data and the reference visual behavior data are compared so as to deduce whether the person visual behavior is adapted with respect to said activity of the person.

Advantageously, the monitoring of the visual behavior of the person appears to be particularly relevant when willing to monitor the behavior of a person carrying out a specific activity.

Indeed, the inventors have observed that the visual behavior of a person may be linked very accurately to the activity carried out by the person.

According to further embodiments which can be considered alone or in combination:
- during the person visual behavior providing step at least part of the person visual behavior data are measured on the person, for example using a head mounted device; and/or
- the method of the invention further comprises:
  - a person head movement data providing step during which person head movement data indicative of the head movement of the person are provided,
  - a reference head movement data providing step during which reference head movement data indicative of the head movement data based on said activity of the person are provided,
  and during the comparing step the person head movement data and the reference head movement data are compared so as to determine whether the head movement of the person corresponds to the reference head movement given the current activity of the person; and/or
- the method further comprises a physiological data providing step during which physiological data indicative to at least one parameter of the physiology of the person are provided and during the reference visual behavior providing step the reference visual behavior data are provided based on the physiology data; and/or
- the activity of the person comprises driving and the method further comprises a driving condition data providing step during which driving condition data indicative of the driving conditions are provided and during the reference visual behavior providing step the reference visual behavior data are provided based on the driving condition data.

The invention further relates to a method for determining a reference visual behavior corresponding to an activity of a person, the method comprising:
- a person visual behavior providing step S31 during which person visual behavior data indicative of the visual behavior of the person are provided,
- a person activity data providing step S32 during which person activity data indicative of the current activity of the person are provided,
- a performance data providing step S33 during which performance data indicative of the performance of the person when carrying out the current activity are provided,
- a recording step S34 during which the value of the person visual behavior data and the performance data are recorded,
- an environment data providing step S312 during which environment data indicative to the environment of the person are provided, wherein the step S31 to S34 and S312 are repeated, for example regularly, and the most adapted visual behavior of the person to the activity is determined based on the recorded values and the environment data.

According to further embodiments which can be considered alone or in combination:
- during at least part of the visual behavior data are measured on the person visual behavior providing step person, for example using a head mounted device; and/or
- the method further comprises a head movement data providing step during which head movement data indicative of the head movement of the person are provided, the head movement data providing step is repeated together with steps S31 to S34 and the most adapted head movement of the person to the activity is determined based on the recorded values; and/or
- the method further comprises an physiological data providing step during which physiological data indicative to at least one parameter of the physiology of the person are provided, the physiological data providing step is repeated together with steps S31 to S34 and the physiological data are considered when determining the most adapted visual behavior of the person to the activity.

The invention further relates to a head mounted device adapted to be mounted on the head of a wearer and comprising:
- at least one sensor configured to sense at least one visual behavior parameter of the wearer; and
- a communication unit configured to communicate data indicative of the at least one sensed parameter to a comparison unit.

The head mounted device according to the invention may further comprise:
- a spectacle frame, and the at least one sensor is mounted on the spectacle frame; and/or
- an optical lens and the at least one sensor is on or within the optical lens; and/or
- a display unit adapted to display a image to the wearer.

The invention also comprises a system for monitoring the visual behavior of a person comprising:
- a communication unit configured to receive person visual behavior data indicative of the visual behavior of the person, person activity data indicative of the current activity of the person, and reference visual behavior data, and
- a comparing unit configured to compare the person visual behavior data and the reference visual behavior data so as to determine whether the person visual behavior is adapted with respect to the current activity of the person.

The system according to the invention may further comprise a head mounted device according to the invention, the communication unit being configured to receive the person visual behavior data indicative of the at least one sensed parameter.

According to a further aspect, the invention relates to a system for monitoring the visual behavior of a person, comprising:
- a memory; and
- a processor arranged to execute a program instructions stored in the memory to:
  - receive person activity data indicative of an activity of the person,
  - receive person visual behavior data indicative of the visual behavior of the person related to said activity of the person,
  - receive a reference visual behavior data indicative of the reference visual behavior of the person based on said activity of the person,
  - compare the person visual behavior data and the reference visual behavior data are compared so as to deduce whether the person visual behavior is adapted with respect to said activity of the person.

The invention further relates to a computer program product comprising one or more stored sequences of instructions that are accessible to a processor and which, when executed by the processor, causes the processor to carry out the steps of the method according to the invention.

The invention also relates to a computer-readable storage medium having a program recorded thereon; where the program makes the computer execute the method of the invention.

The invention further relates to a device comprising a processor adapted to store one or more sequence of instructions and to carry out at least one of the steps of the method according to the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method.

The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

Elements in the figures are illustrated for simplicity and clarity and have not necessarily been drawn to scale. For example, the dimensions of some of the elements in the figure may be exaggerated relative to other elements to help improve the understanding of the embodiments of the present invention.

Figure 1:
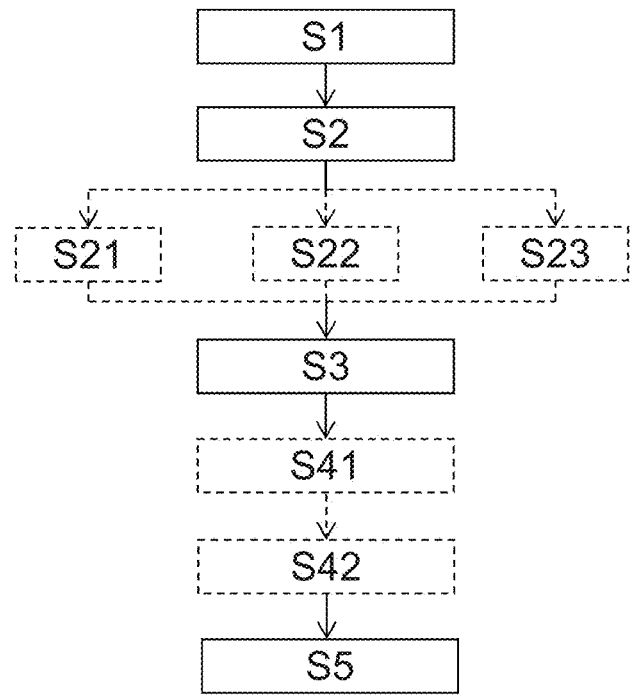
FIG. 1 is an illustration of a chart-flow of a monitoring method according to the invention.

As illustrated on FIG. 1, the method for monitoring the visual behavior of a person according to the invention, comprises at least:

a person activity data providing step S1,
a person visual behavior data providing step S2,
reference visual behavior providing step S3, and
a comparing step S4.

Person activity data indicative of an activity of the person are provided during the person activity data providing step S1.

The person activity data may identify directly an activity carried out by the person or may be data allowing determining such activity, for example an indication allowing determining the activity of the person from a data base and/or lookup table.

The person activity data may be provided directly by the person itself, for example by selecting an activity in a list of activities.

Furthermore, the person activity data may be determined based on analysis of data provided by sensors that measure the wearer's behavior or the environment of the wearer.

The activity that may be identified may be for example, but not limited to driving, sport, playing golf, playing tennis, practicing archery, reading, walking, paragliding, etc. . . .

During the person visual behavior data providing step S2, person visual behavior data indicative of the visual behavior of the person related to the activity of the person are provided.

The person visual behavior may at least partly be provided by the person itself or correspond to measurements carried out on the person.

According to an embodiment of the invention, at least part of the person visual behavior data are measured on the person, for example using a head mounted device.

The visual behavior data may provide indication relating to the gazing behavior of the person, such as gazing direction, gazing distances, variation of gazing distances.

The visual behavior data may further relate to oculomotor parameters of the person, such as eye movements, saccades, accommodation, convergence.

The visual behavior data may further relate to ocular parameters of the person, such as opening of the eyelid, pupil diameter, blink frequency, duration of the blink, and strength of the blink.

During the reference behavior providing step S3, a reference visual behavior data indicative of the reference visual behavior of the person based on the activity data is provided.

In other words, based on the identified activity of the person a reference visual behavior of that person for such identified activity is provided. The reference visual behavior data may be provided from a data base or a look-up table either specific to the person or adapted for an average person. As illustrated in FIG. 1, the method of the invention may further comprise an environment data providing step S21 during which environment data indicative of the environment of the person are provided. The reference visual behavior data may be provided based at least partly on the environment data.

The environment data may relates to any parameter of the environment of the person that may have an impact on the visual behavior of the person, in particular on the reference visual behavior of the person.

For example, the environment data may relate to spectral features and intensity of the light received by the person.

Furthermore, the environment data may relate to temperature, wind speed, and/or humidity of the environment of the person, the amount and/or the type of allergens and/or pollutants contained in the environment of the person and/or an indication of the localization of the person such as indoor or outdoor and/or the place of carrying out the activity of the person, proximity to relief and/or water, etc. . . .

As illustrated in FIG. 1, the method of the invention may further comprise a physiological data providing step S22 during which physiological data indicative of at least one parameter of the physiology of the person are provided. The reference visual behavior data may be provided based at least partly on the physiological data.

The physiological data may relate to any physiological parameter of the person that may have an impact on the visual behavior of the person, in particular on the reference visual behavior of the person.

For example, the physiological data may relate to the ametropia of the person and/or features of the eyes of the person such as eye color, pupil diameter, and/or the age, and/or the height and/or the weight of the person.

The method of the invention may be particularly advantageous, when the activity of the person comprises driving.

As illustrated in FIG. 1, the method of the invention may further comprise a driving condition data providing step S23 during which driving condition data indicative of the driving conditions are provided. The reference visual behavior data may be provided based at least partly on the driving condition data.

Typically, the driving condition may relate to the speed of the car and/or the traffic conditions.

During the comparing step S5, the person visual behavior data and the reference visual behavior data are compared so as to deduce whether the person visual behavior is adapted with respect to the activity of the person.

Further to the comparing step S5, the method may comprise an information providing step during which information based on the comparison of the person visual behavior data and the reference visual behavior data is provided either to the person or to a third party.

For example, the information comprises a recommendation and/or access to a service.

The information data may provide access to a service or functionality among which, but not limited to:
 alert a third party, such as a medical center,
 provide a feed back to the person,
 propose complementary solution and as an advice on the behavior of the wearer or offer specific training tools,
 knowledge of the physiological parameters in relation to the environment for the person or for the environment or for medical personnel or sports coach,
 monitoring adherence to the visual behavior requested by a coach,
 provision of support/compare/to create social ties (eg via a forum, aggregated databases) disseminate best practices, . . .
 evidence of the effectiveness/quality of the system used.

As illustrated on FIG. 1, the method of the invention may further comprise:
 a person head movement data providing step S41, and
 a reference head movement data providing step S42.

Person head movement data indicative of the head movement of the person are provided during the person head movement data providing step S41. The person head movement data may be measured using sensor of a head mounted device such as a head mounted device equipment with an accelerometer and/or gyroscope configured to sense the movement and/or orientation of the head mounted device.

Reference head movement data indicative of the head movement data based on said activity of the person are provided during the reference head movement data providing step S42.

Advantageously, the head movements of a person can be correlated to the body movement of such person. Therefore, the head movement data may be used to determine general movement of the body of the person.

During the comparing step S5, the person head movement data and the reference head movement data are compared so as to determine whether the head movement of the person corresponds to the reference head movement given the current activity of the person.

The invention further relates to a method for determining a reference visual behavior corresponding to an activity of a person.

Figure 2:
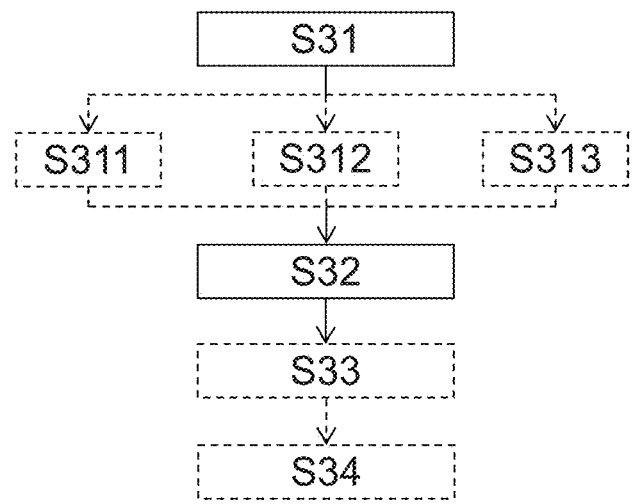
FIG. 2 is an illustration of a chart-flow of a method for determining a reference visual behavior according to the invention.

As illustrated on FIG. 2, such method may comprise:
- a person visual behavior providing step S31,
- a person activity data providing step S32,
- a performance data providing step S33, and
- a recording step S34

Person visual behavior data indicative of the visual behavior of the person are provided during the person visual behavior providing step S31. Typically, the person visual behavior data may be of any type described in reference to the monitoring method. According to a preferred embodiment, the person visual behavior data are measured on the person, for example using a head mounted device.

Person activity data indicative of the current activity of the person are provided during the person activity data providing step S32. The activity that may be identified by the person activity data are of any type described in reference to the monitoring method.

Performance data indicative of the performance of the person when carrying out the current activity are provided during the performance data. Typically, the performance data correspond to a score determined objectively and/or subjectively relating to the manner in which the person carries out the activity.

During the recording step S34, the value of the person visual behavior data and the performance data are recorded.

The steps S31 to S34 are repeated, for example regularly, and the most adapted visual behavior of the person to the activity is determined based on the recorded values.

According to an embodiment of the invention illustrated on FIG. 2, the method for determining a reference visual behavior may further comprises a head movement data providing step S311 during which head movement data indicative of the head movement of the person are provided. The head movement data providing step S311 is repeated together with steps S31 to S34 and the most adapted head movement of the person to the activity is determined based on the recorded values.

According to an embodiment of the invention illustrated on FIG. 2, the method for determining a reference visual behavior may further comprises an environment data providing step S312 during which environment data indicative to the environment of the person are provided.

The environment data may be of any type described in reference to the monitoring method.

The environment data providing step S312 is repeated together with steps S31 to S34 and the environment data are considered when determining the most adapted visual behavior of the person to the activity.

According to an embodiment of the invention illustrated on FIG. 2, the method for determining a reference visual behavior may further comprises a physiological data providing step S313 during which physiological data indicative to at least one parameter of the physiology of the person are provided.

The physiological data may be of any type described in reference to the monitoring method.

The physiological data providing step S313 is repeated together with steps S31 to S34 and the physiological data are considered when determining the most adapted visual behavior of the person to the activity.

The invention further relates to a head mounted device adapted to be mounted on the head of a wearer and comprising:
- at least one sensor configured to sense at least one visual behavior parameter of the wearer; and
- a communication unit configured to communicate data indicative of the at least one sensed parameter to a comparison unit.

Figure 3:
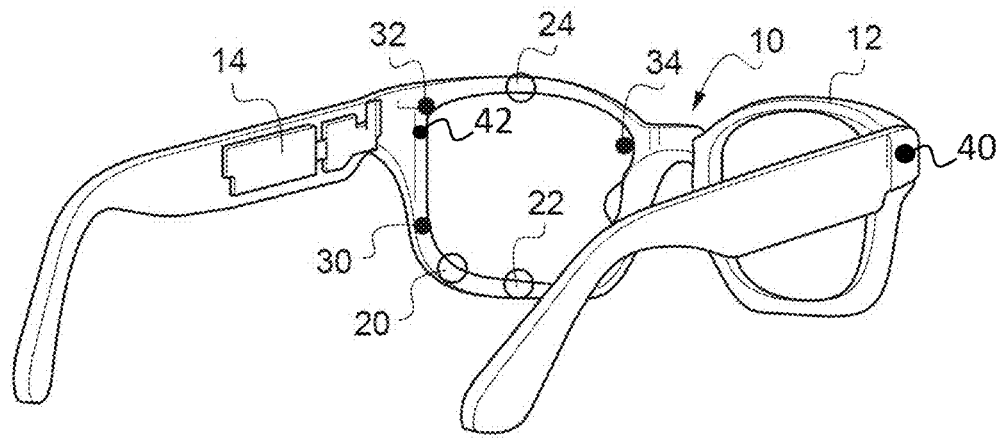
FIG. 3 represents a head mounted device according to the invention.

An example of head mounted device is illustrated on FIG. 3. The head mounted device 10 represented on FIG. 3 comprises a spectacle frame 12 with three cameras 20, 22, 24 directed at the left eye (not shown) of the wearer. The cameras 20, 22, 24 are arranged to be directed toward the head in order to track the locations of the eyes of the wearer and/or the structures of the eyes of the wearer, for example the pupils, eyelids, irises, glints, and/or other reference points in the region of the eye(s).

The cameras 20, 22, 24 may include charge-coupled device (CCD), complementary metal-oxide-semiconductor (CMOS), or other photodetectors that include an active area, e.g., including a rectangular or linear or other array of pixels, for capturing images and/or generating video signals representing the images. The active area of each of the cameras 20, 22, 24 may have any desired shape, e.g., a square or rectangular shape, circular, and the like. The surface of the active area of one or more cameras may also be curved, if desired, e.g., to compensate during image acquisition for the nearby three-dimensional curvature of the eye and surrounding structures being imaged.

The head mounted device 10 further comprises three illumination sources 30, 32, 34 arranged so as to illuminate the left eye of the wearer when wearing the spectacle frame 12.

The three illumination sources 30, 32, 34 are fixed to the spectacle frame 12. In an exemplary embodiment, illumination sources 30, 32, 34 may include light-emitting diodes (LEDs), organic LEDs (OLEDs), laser diodes, or other devices that convert electrical energy into photons. Each illumination source 30, 32, 34 may be used to illuminate the eye to acquire images using any of the cameras 20, 22, 24 and/or to produce reference glints for measurement purposes to improve gaze-tracking accuracy. In an exemplary embodiment, each light source 30, 32, 34 may be configured for emitting a relatively narrow or wide bandwidth of the light, for example infrared light at one or more wavelengths between about 700-1000 nanometers. For example, AlGaAs LEDs provides an emission peak at 850 nm and are widely used and affordable, while commodity CMOS cameras used in mobile phones and webcams show a good sensibility at this wavelength.

The head mounted device 10 further comprises a communication unit 14 configures to communicate data indicative of the visual behavior if the user of the head mounted device to a comparison unit.

Although not represented, the eye tracking device further comprises a power source, for example a battery and/or other electronics.

Advantageously, the power source and/or other electronics may be arranged on the same side of the spectacle frame than the communication unit 14 so as to facilitate the integration of the electronics devices on the spectacle frame.

Although on FIG. 3 cameras and illumination sources have been represented only on the left side of the spectacle frame, the eye tracking device may very well comprise cameras and illumination sources and/or on the right side of the spectacle frame.

Advantageously, having cameras on both sides of the spectacle frame allows providing accurate information on the gazing direction and distance of the wearer.

For example, such eye tracking device can be used for long periods of time so as to determine accurately in everyday life conditions the visual behavior of the wearer.

Furthermore, although on FIG. 3, the sensors have been represented on the spectacle frame, such sensors may be on or within the optical lenses.

Although the mounted sensing device has been described with eye trackers, the mounted sensing device may comprise other type of sensors, such as photodiodes.

As represented on FIG. 3, the mounted sensing device may comprise a sensor 40 configured to sense environment parameters and/or a sensor configured to sense ocular parameters of the eye of the wearer such as blink frequency, and/or an sensor, not represented, on the bridge of the spectacle frame facing in front of the wearer of the frame configured to measure the gazing distance, and/or a sensor configure to measure the luminosity of the environment.

The monitoring of the visual behavior of the user of the head mounted device requires having a communication unit 14 configured to communicate data indicative of the at least senses parameter a comparison unit.

The comparison unit is typically included in a system for monitoring the visual behavior. Such system comprising:
- a communication unit configured to receive person visual behavior data indicative of the visual behavior of the person, person activity data indicative of the current activity of the person, and reference visual behavior data, and
- a comparing unit configured to compare the person visual behavior data and the reference visual behavior data so as to determine whether the person visual behavior is adapted with respect to the current activity of the person.

The monitoring system may be integrated in the head mounted device so as to have an embedded system.

According to an embodiment of the invention, the communication unit may be configured to receive data from different sensing devices. Typically, data relating to the environment or the activity of the person may be provided from a distant sensing device, for example mounted in a car, a golf club, a bow or any mounted sensing device that the person may carry such as a watch, shoes, close, clothes, a hat etc. . . .

Furthermore the communication unit may receive data form a data base and/or look-up table.

Figure 4:
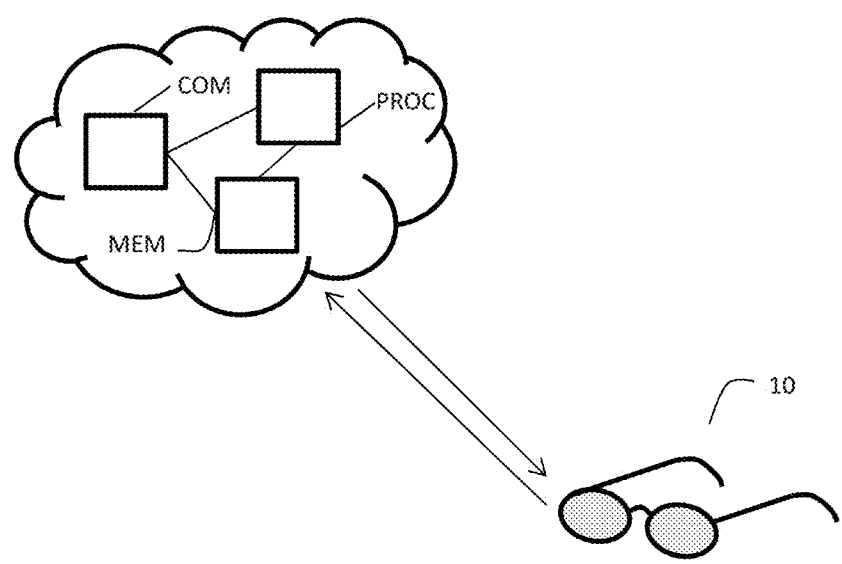
FIG. 4 represents a networked data-processing device according to the invention.

According to an embodiment of the invention, illustrated on FIG. 4, the head mounted device communicates with a distant entity that comprises a monitoring system. Communication can be done through different communication devices and protocols, like Bluetooth, Zigbee, WiFi or others.

For example, the communication unit is configured to communicate with the distance entity either to store the measured features in a memory MEM or to provide an information indicative of the visual behavior of the head mounted device and the user of the head mounted device.

Typically, the distance entity comprises a communication unit COM configured to communicate at least with the head mounted device, a memory MEM, at least one processor PROC and program instructions stored on a non-transitory computer-readable medium and executable by the at least one processor to execute the step of the monitoring method of the invention.

The distance entity can include different computing objects such as personal digital assistants, audio/video devices, mobile phones, MPEG-1 Audio Layer 3 (MP3) players, personal computers, laptops, tablets, bluetooth headset, watch, wristband, etc. . . .

Each computing object and the head mounted device can communicate with one or more other by way of a communication network, either directly or indirectly. Even though illustrated as a single element in FIG. 4, network can include other computing objects and computing devices that provide services to the system of FIG. 4, and/or can represent multiple interconnected networks, which are not shown.

In a network environment in which the communications network/bus can be the Internet, the computing objects can be Web servers, file servers, media servers, etc. with which the client computing objects or devices communicate via any of a number of known protocols, such as the hypertext transfer protocol (HTTP).

Figure 5:
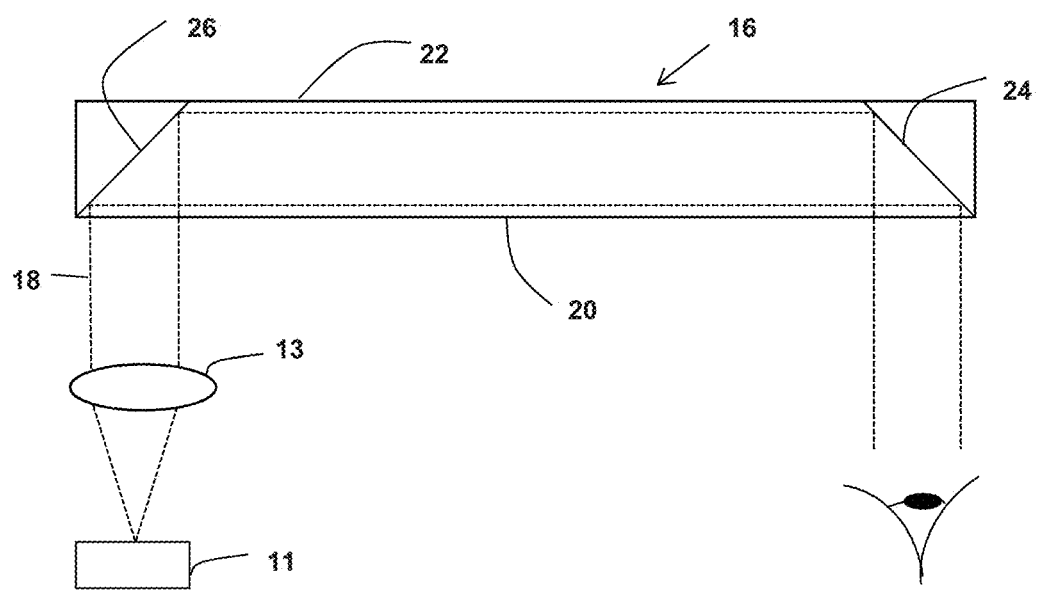
FIG. 5 is a schematic representation of a head mounted device according to a further embodiment of the invention.

As represented on FIG. 5, the head mounted device according to the invention may comprise a virtual image display device, preferably allowing the wearer to see both the virtual image and the real world through it. The virtual image display device is able to display graphical images, and an electronic driving system (memory+processor) sends to the virtual display image the image to display. Preferably it is able to display image in different viewing directions, and this displaying direction and the position of the field of view, can be adapted from the relative position measured by the sensors. Furthermore, the image to be displayed can be modified depending of the visual behavior measured by the sensors.

Information concerning the adaptation of the visual behavior of the person may be provided to the person or a third party as visual indications and/or audio indications, and/or tactile indications such as vibrations.

An example of see-through display system is illustrated in FIG. 5. Such see-trough display system comprises a display source 11, a collimating device 13, and an optical insert 16 constituted by a light-guide optical element 16 (LOE).

The display source 11 can be emissive or not emissive.

The light-guide optical element 16 typically includes at least two major surfaces 20 and 22 and edges, at least one partially reflecting surface 24 and an optical element 26 for coupling light thereinto. The output waves 18 from the collimating device 13 enter the light-guide optical element 16 through its lower surface 20. The incoming waves (towards the light-guide optical element 16) are reflected from the surface 26 and trapped in the light-guide optical element 16.

In an embodiment, the electro-optical system may comprise a plane light-guide optical element 16 with at least two planes major surfaces 20 and 22. For example, such a light guide optical element 16 may be one of Lumus Company.

In an alternative embodiment, the electro-optical system may comprise a curved light-guide optical element 16.

The light-guide may be encapsulated in an optical lens or placed in front of an optical lens.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for monitoring the visual behavior of a person, the method comprising:
   receiving person activity data indicative of an activity of the person;
   receiving person visual behavior data indicative of the visual behavior of the person related to said activity of the person;
   receiving environment data indicative of the environment of the person;
   receiving reference visual behavior data indicative of a reference visual behavior of the person based on said activity of the person and the environment data; and
   comparing the person visual behavior data and the reference visual behavior data to deduce whether the person visual behavior is adapted for said activity of the person, wherein
   the receiving of the person visual behavior data comprises receiving the person visual behavior data from a head mounted device that measures at least part of the person visual behavior data.

2. The method according to claim 1, further comprising:
   receiving person head movement data indicative of the head movement of the person;
   receiving reference head movement data indicative of the head movement data based on said activity of the person; and
   comparing the person head movement data and the reference head movement data to determine whether the head movement of the person corresponds to the reference head movement given the current activity of the person.

3. The method according to claim 1, wherein
   the environment data relate to spectral features and intensity of the light received by the person.

4. The method according to claim 1, further comprising receiving physiological data indicative of at least one parameter of the physiology of the person, wherein receiving the reference visual behavior comprises receiving the reference visual behavior data based on the physiology data.

5. The method according to claim 1, wherein
   the activity of the person comprises driving and the method further comprises receiving driving condition data indicative of driving conditions, wherein the reference visual behavior data are provided based on the driving condition data.

6. A method for determining a reference visual behavior corresponding to an activity of a person, the method comprising:
   receiving person visual behavior data indicative of a visual behavior of the person;
   receiving person activity data indicative of a current activity of the person;
   receiving performance data indicative of the performance of the person when carrying out the current activity;
   recording values of the person visual behavior data and the performance data;
   receiving environment data indicative of the environment of the person, the environment data corresponding to spectral features and intensity of the light, and/or temperature, and/or wind speed, and/or humidity of the environment, and/or the amount and/or type of allergens and/or pollutants contained in the environment, and/or indicator of the location of the person, and/or the place of carrying out the activity; and
   determining a most adapted visual behavior of the person to the activity based on the recorded values and the environment data, wherein
   the receiving of the person visual behavior data comprises receiving the person visual behavior data from a head mounted device that measures at least part of the person visual behavior data.

7. The method according to claim 6, further comprising:
   receiving head movement data indicative of a head movement of the person, and
   determining a most adapted head movement of the person to the activity based on the recorded values.

8. The method according to claim 6, further comprising receiving physiological data indicative of at least one parameter of a physiology of the person, wherein determining the most adapted visual behavior of the person to the activity is based on the physiological data.

9. A system for monitoring the visual behavior of a person, comprising:
   a memory; and
   a processor configured to execute program instructions stored in the memory to:
     receive person activity data indicative of an activity of the person;
     receive person visual behavior data indicative of a visual behavior of the person related to said activity of the person;
     receive reference visual behavior data indicative of a reference visual behavior of the person based on said activity of the person;
     compare the person visual behavior data and the reference visual behavior data to deduce whether the person visual behavior is adapted for said activity of the person, wherein
     receiving of the person visual behavior data comprises receiving the person visual behavior data from a head mounted device that measures at least part of the person visual behavior data.

10. The system according to claim 9, wherein
    the processor is further configured to execute the program instructions stored in the memory to receive environment data indicative of the environment of the person.

11. The system according to claim 9, wherein
    the processor is further configured to execute the program instructions stored in the memory to:
    receive head movement data indicative of a head movement of the person from the head mounted device;
    receive reference head movement data indicative of the head movement data based on said activity; and
    compare the person head movement data and the reference head movement data to determine whether the head movement of the person corresponds to the reference head movement given the current activity of the person.

12. The system according to claim 10, wherein
    the environment data relate to spectral features and intensity of the light received by the person.

13. The system according to claim 9, wherein
the processor is further configured to execute the program instructions stored in the memory to receive physiological data indicative of at least one parameter of the physiology of the person.

14. The system according to claim 13, wherein
the reference visual behavior data are provided based the physiology data.

15. The system according to claim 9, wherein
the activity of the person comprises driving.

16. The system according to claim 15, wherein
the processor is further configured to execute the program instructions stored in the memory to receive driving condition data indicative of driving conditions.

\* \* \* \* \*